US00PP19082P3

(12) United States Plant Patent
Dirr

(10) Patent No.: US PP19,082 P3
(45) Date of Patent: Aug. 12, 2008

(54) ***HYDRANGEA PANICULATA* PLANT NAMED 'HYPMAD I'**

(50) Latin Name: *Hydrangea paniculata*
Varietal Denomination: HYPMAD I

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 313 days.

(21) Appl. No.: 11/337,831

(22) Filed: Jan. 23, 2006

(65) Prior Publication Data

US 2007/0283467 P1 Dec. 6, 2007

(51) Int. Cl.
*A01H 5/00* (2006.01)

(52) U.S. Cl. ..... Plt./250

(58) Field of Classification Search ..... Plt./250
See application file for complete search history.

*Primary Examiner*—Annette Para
(74) *Attorney, Agent, or Firm*—Greenlee Winner and Sullivan, PC

(57) ABSTRACT

*Hydrangea paniculata,* 'HYPMAD I' has full glistening white inflorescences that mature to parchment. The habit is compact, rounded with strong, stout stems that hold the flowers upright. The leathery, dark green leaves are heat, drought, insect and disease resistant.

3 Drawing Sheets

Botanical classification: *Hydrangea paniculata.*
Varietal denomination: 'HYPMAD I'.

BACKGROUND OF THE INVENTION

The present invention relates to a new and distinct cultivar of *Hydrangea paniculata,* a member of the Hydrangeaceae family, hereinafter referred to as 'HYPMAD I'. This cultivar is grown primarily as an ornamental for landscape use and for use as fresh cut and dried flowers. The cultivar originated from open-pollination of *Hydrangea paniculata* 'Pink Diamond' (unpatented), the pollen door being unknown. It was selected at the University of Georgia, Athens, Ga. in 2001, from the progeny seedlings of this open pollination by continued evaluation for large, glistening white sepals that cover the interior fertile flowers, stout stems that hold the paniculate inflorescences upright, leathery, dark green, heat and drought tolerant foliage, and compact growth habit.

'HYPMAD I' is distinguished from its female parent 'Pink Diamond' by its sepals (sterile florets) that form a solid white panicle and completely cover the fertile interior flowers. The sepals emerge light green, open glistening white, and mature green to parchment, maintaining the latter color when utilized as dried flowers. The sepals never develop the pronounced pink color of 'Pink Diamond'. 'HYPMAD I' has stout, thickish stems that hold the inflorescences upright, whereas in side-by-side comparisons, 'Pink Diamond' inflorescences splay and bend.

'HYPMAD I' has leathery, thick, dark green leaves that are more heat and drought resistant than the lighter green, thinnish leaves of 'Pink Diamond'. 'HYPMAD I' develops a compact growth habit, 120 cm by 160 cm after 4 years, whereas 'Pink Diamond' was 185 cm by 185 cm at the same age in side-by-side comparisons.

'HYPMAD I' holds its inflorescences more upright than many *H. paniculata* varieties, and the inflorescence is denser, more completely covered with sterile florets, than most, and it does not mature to a pink color of the dense inflorescence types such as 'Grandiflora' (unpatented), 'Webb's' (unpatented) or 'Little Lamb' (unpatented).

SUMMARY OF THE INVENTION

The following traits have been observed and represent the characteristics of the new Cultivar. In combination these characteristics distinguish 'HYPMAD I' from all other varieties in commerce known to the inventor.

1. Glistening white sepals of the sterile florets cover the fertile flowers producing a showy, full paniculate inflorescence.
2. At maturation, sepals turn green to parchment and dry to the latter color.
3. Thick stout stems hold the inflorescences upright even after rain and wind.
4. Thick, leathery, dark green leaves display increased heat, drought, insect, and disease tolerances.
5. Compact, dense habit, 120 cm high by 160 cm in four years under field conditions in Athens, Ga.

'HYPMAD I' has been asexually propagated in Athens, Ga. since 2001. The characteristics of the Cultivar have been stable and reproduced true-to-type in successive generations.

DESCRIPTION OF THE PHOTOGRAPHS

BOTANICAL DESCRIPTION OF THE PLANT

Figure 1:
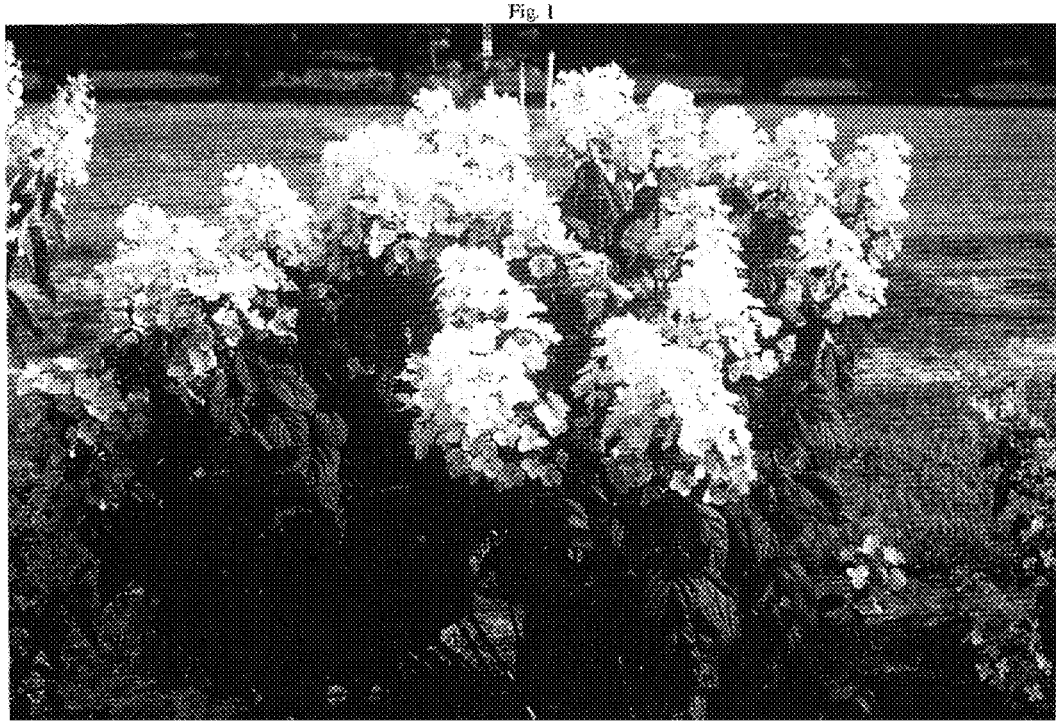
FIG. 1 shows a 4-year-old unpruned plant in the ground at Athens, Ga., taken Jul. 23, 2005 showing the richness of the white inflorescences, the strong upright stems and the dark green leaves.
Figure 2:
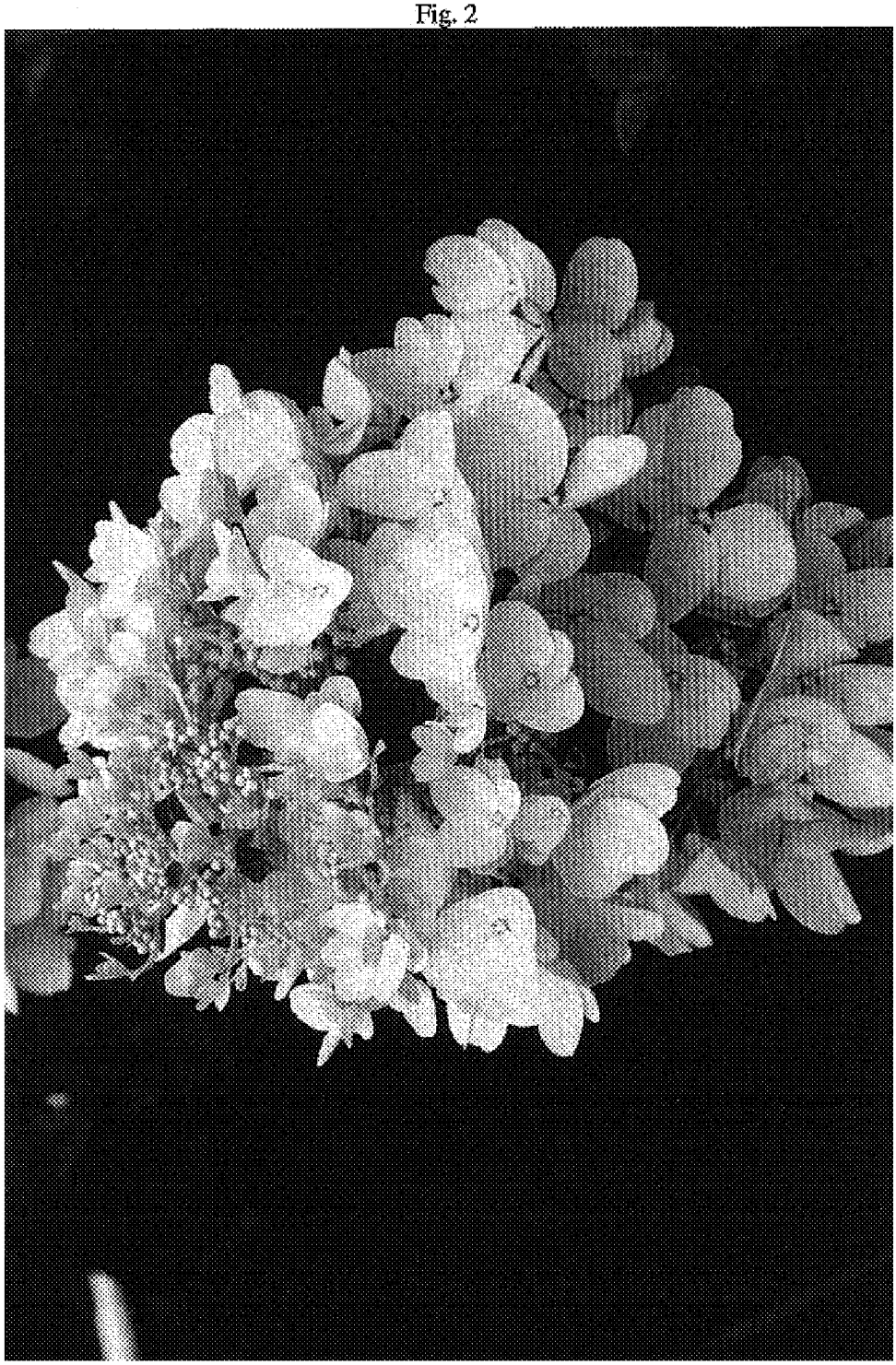
FIG. 2 shows an inflorescence approaching full expression, showing how the sepals cover the fertile flowers.
Figure 3:
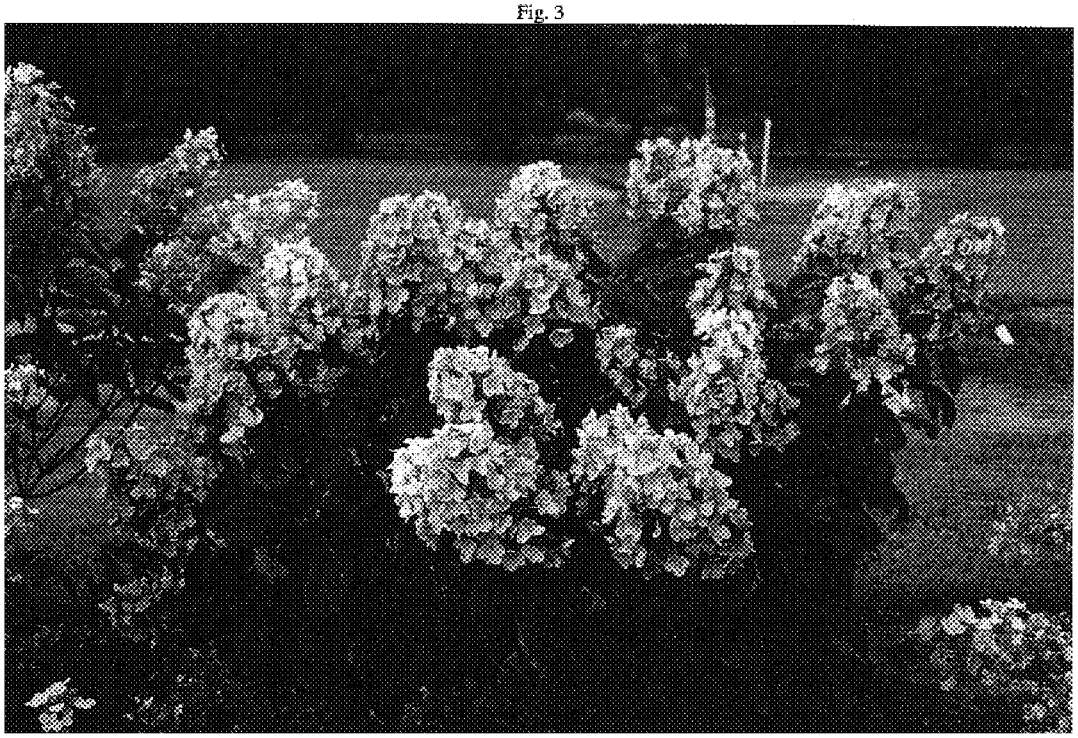
FIG. 3 shows a 4-year-old unpruned plant in the ground at Athens, Ga., taken Aug. 10, 2005, showing the inflorescences turning green to parchment.

A detailed description of *Hydrangea paniculata* 'HYPMAD I' follows. Colors are based on The Royal Horticultural Colour Chart (1995). All measurements/characteristics were taken from 4-year-old plants in the ground at the UGA Horticultural Farm, Athens, Ga. USDA Zone 7. Measurements of leaf/stems and floral characteristics are based on 10 to 20 samples.

Plant:

The plant has a compact, upright, rounded growth habit, with many upright branches from the base, attaining a size of 120 cm high by 160 cm wide after 4 years.

Stems:

The current year stems are round, averaging 7.6 mm in diameter, with no pubescence or exfoliation and are Greyed—Green 197C in color. The average length of the internode is 5.1 cm. Older stems are up to 21.3 mm in diameter, with a rough texture, and Greyed—Green 197B in color.

Vegetative buds:

The imbricate vegetative buds are in an opposite arrangement, 1 per leaf and 2 per node, flat on the stem. They are rounded to globose in shape, 1 mm by 1 mm, and have 4 to 6 scales which are Brown 200B in Color.

Flower buds:

The flower buds are round in shape with no pubescence, 3 mm long by 3 mm wide and White 155B in color. They develop in the summer and the time range for showiness is 8 weeks.

Leaf:

The leaves, in opposite arrangement, are ovate in shape with rounded to acute base and acute apex and finely serrate margin. The mature leaf is 12.9 cm long by 7.5 cm wide, thick and leathery with no wax. It is finely setose on upper and lower surfaces, and heavily setose on lower veins and midrib. The color of the emerging leaf is Yellow—Green 144A on both upper and lower surfaces, maturing to Green 139A on the upper surface and Greyed—Green 191A on the lower. The venation is pinnate, with Yellow—Green 148D veins.

The petioles average 2.6 cm long and 3.3 mm in diameter, are grooved above and rounded below, finely setose, and are Yellow—Green 146D in color.

Inflorescence:

The bloom period is 2 months from flower opening to maturity. The paniculate inflorescence, containing an average of 721 sterile florets (sepals) and fertile flowers, averages 21.2 cm long by 16.7 cm at greatest width.

There are on average 18 inflorescences per plant, one per terminal branch.

Sterile florets:

There are 4 sepals, elliptical to round in shape with obcordate apex and rounded base and entire margin. The texture is smooth with no pubescence. They are 29.4 mm long by 24.6 mm wide. At emergence, the upper and lower surfaces are Yellow—Green 154D, becoming White 155C at full bloom, and Yellow—Green 145A with tinges of Greyed—Red 181B to 181C on upper surface and a Yellow—Green 145B lower surface at maturity.

The peduncle is finely setose and Yellow—Green 150D in color.

Fertile flowers:

The petals are ovate in shape, with acute apex, truncate base and an entire margin. They are 3 mm in length by 2 mm wide, with a smooth texture and no pubescence. Their color is White 155C.

The pedicel is 1.2 mm long, finely setose, and Green—White 157A in color.

There are 10 anthers, 0.75 mm long by 0.5 mm wide and Greyed—Orange 165B in color.

The filament is 3 mm long by 0.5 mm wide and White 155C in color.

The superior pistil is globose in shape, 4 mm long by 2 mm wide with no pubescence and Yellow—White 158C/Yellow—Green 145C in color.

There are 3 stigmas per flower, with no pubescence and White 155C in color.

The style is columnar in shape, 2 mm long with no pubescence and White 155C in color.

There is 1 ovary, rounded in shape, with no pubescence.

Fruit:

The fruit is a dehiscent capsule, ovoid in shape, 4 mm long by 3 mm wide, and maturing from Yellow—Green 145B through Greyed—Orange 176A to Brown 200A in color. They are persistent for 3 to 4 months but are not aesthetic.

Seed:

The seeds are linear in shape, 3 mm long by 0.5 mm wide and Greyed—Orange 165B in color.

I claim:

1. A new and distinct variety of *Hydrangea paniculata* plant substantially as herein described and illustrated.

* * * * *